United States Patent [19]

Matkovich et al.

[11] Patent Number: 5,219,101

[45] Date of Patent: Jun. 15, 1993

[54] CONTAMINATION-RESISTANT DISPENSING AND METERING DROP FORMING DEVICE

[75] Inventors: Vlado I. Matkovich, Glen Cove, N.Y.; Thomas E. Schlaudecker, Hamilton Square, N.J.; Martin W. Henley, New Hope, Pa.; Thomas Bormann, Seaford, N.Y.

[73] Assignees: Pall Corporation, Glen Cove, N.Y.; Merck & Co., Inc., Rahway, N.J.

[21] Appl. No.: 642,158

[22] Filed: Jan. 17, 1991

Related U.S. Application Data

[63] Continuation of Ser. No. 360,041, Jun. 1, 1989, abandoned.

[51] Int. Cl.⁵ .............................................. B67D 5/58
[52] U.S. Cl. .................................... 222/189; 222/212; 222/420; 210/321.64; 210/321.84; 604/295
[58] Field of Search ............... 222/189, 420, 421, 206, 222/212; 604/126, 295, 298; 210/321.64, 321.84, 500.38, 500.42

[56] References Cited

U.S. PATENT DOCUMENTS

| | | |
|---|---|---|
| 2,263,890 | 11/1941 | Salvesen . |
| 2,806,637 | 9/1957 | Wallingford . |
| 2,987,223 | 6/1961 | Armour ........................ 222/420 X |
| 3,149,758 | 9/1964 | Bush et al. ........................ 222/189 |
| 3,189,223 | 6/1965 | Mackal ........................ 222/420 X |
| 3,241,731 | 3/1966 | Bright et al. . |
| 3,248,017 | 4/1966 | Allen ........................ 222/420 |
| 3,449,081 | 6/1969 | Hughes ........................ 222/189 X |
| 3,631,654 | 1/1972 | Riely . |
| 3,645,262 | 2/1972 | Harrigan . |
| 3,760,987 | 9/1973 | Meterhoefer ........................ 222/189 X |
| 4,002,168 | 1/1977 | Petterson ........................ 604/298 |
| 4,093,124 | 6/1978 | Morane et al. ........................ 222/189 X |
| 4,203,848 | 5/1980 | Grandine, II ........................ 210/490 |
| 4,319,996 | 3/1982 | Vincent et al. ........................ 210/477 X |
| 4,463,880 | 8/1984 | Kramer et al. ........................ 222/420 X |
| 4,471,890 | 9/1984 | Dougherty ........................ 222/420 X |
| 4,533,068 | 8/1985 | Meierhoefer ........................ 222/189 |
| 4,797,259 | 1/1989 | Matkovich et al. ........................ 422/101 |
| 4,915,839 | 4/1990 | Marinaccio et al. ........ 210/500.38 X |
| 4,917,271 | 4/1990 | Kanner et al. ........................ 222/189 |
| 4,938,389 | 7/1990 | Rossi et al. ........................ 222/189 |
| 4,968,310 | 11/1990 | Menchel et al. . |
| 5,040,706 | 8/1991 | Davis et al. . |

FOREIGN PATENT DOCUMENTS

| | | |
|---|---|---|
| 167562 | 1/1951 | Austria . |
| 0190558 | 8/1986 | European Pat. Off. . |
| 3628197 | 2/1988 | Fed. Rep. of Germany . |
| 661203 | 3/1964 | Italy . |
| 8807359 | 10/1988 | PCT Int'l Appl. . |
| 1067285 | 5/1967 | United Kingdom . |
| 2021429 | 12/1979 | United Kingdom . |
| 2132989 | 7/1984 | United Kingdom . |

*Primary Examiner*—Robert P. Olszewski
*Assistant Examiner*—Boris Milef
*Attorney, Agent, or Firm*—Leydig, Voit & Mayer

[57] ABSTRACT

A device for dispensing liquids in drop form of substantially uniform size is provided which includes a container having a dropper tip including a passageway for ingress of air to and egress of liquid from the device, the passageway communicating between the container and an orifice in the dropper tip; means for temporarily reducing the volume of the container; and, disposed within the dropper tip, across the passageway, a microporous composite membrane with pores of a size to resist passage of contaminants. The membrane has a liquophilic component which permits delivery of drops of a liquid to a desired location outside the container and a liquophobic component which is adapted to resist the passage of such liquid but to permit the passage therethrough of air. Both the liquophilic and liquophobic components of the membrane (which intersects the passageway) communicate with the passageway. The surface area and pore size of the liquophilic component is so selected as to meter liquid being dispensed in drop form and avoid a stream of liquid from emerging from the dropper tip during normal use.

25 Claims, 2 Drawing Sheets

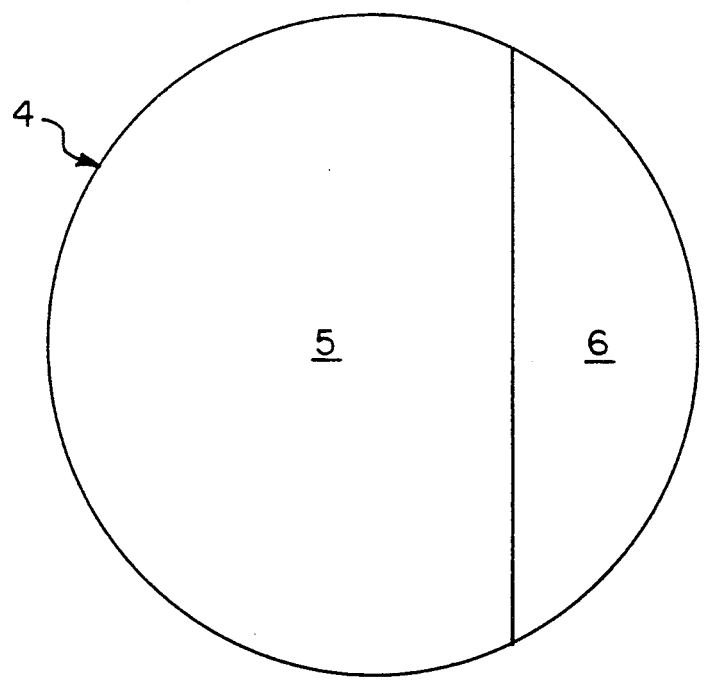

CONTAMINATION-RESISTANT DISPENSING AND METERING DROP FORMING DEVICE

This application is a continuation of application Ser. No. 07/360,041, filed Jun. 1, 1989, now abandoned.

TECHNICAL FIELD

This invention relates to a liquid dispensing and metering device that is especially useful in, for example, the dispensing of optical drugs that typically need to be dispensed in drop form. The present invention provides such a device that also protects the solution from contamination while retained in the device.

BACKGROUND OF THE INVENTION

This invention has wide application in situations where a liquid is required to be dispensed in metered amounts at regular intervals from a container and in which it is critical that contamination from outside, whether particulate or bacterial in nature, be excluded. This is most frequently encountered in the context of the dispensing of medicines such as ophthalmic medicines but the utility of the invention extends to the protection of any liquid against particulate contamination. For ease of understanding, however, the invention will be described primarily in the context of the application that, as is presently anticipated, will be the most commercially attractive.

Many drugs, particularly those used in treatment of various eye disorders, are administered in drop form. The drops are intended to free-fall onto the eye surface, where they distribute across the exposed eye. Dosage of these ophthalmic drugs is often crucial: lower than prescribed levels can result in failure of the treatment and consequent progression of the disease, higher levels can result in untoward side effects that can also interfere with successful resolution.

Complicating the administration of these drugs is the fact that they are often required several times a day and thus, to be practical, must be applied by the patients themselves and not by medical personnel who are formally trained in drug delivery. Patient administration of such drugs has resulted in two serious problems which must be solved for these medications to be successfully used: container contamination and flow rate.

CONTAINER CONTAMINATION

The possibility that bacterial contamination may enter the drug container and proliferate there is an ever-present problem that can destroy the utility of the medicine. This can be the result of dropper contact with a non-sterile surface, such as a body part, or by some other mechanism.

The problem can be most readily understood in the context of the administration of drops of an ophthalmic medicine. Ideally, the pendant drop formed at the tip of the conventional dropper container when the container is squeezed should be allowed to free-fall to the surface of the eye. In addition, the distance between the dropper tip and the surface of the eye should be kept reasonably close. This is important so that the momentum acquired by the free-falling drop will not be so great as to encourage the drop to splatter on impact with the eye surface and thus be substantially lost to the outer surface of the lids and face. Where administration is by a trained professional, it is relatively easy to ensure that the free-falling drop is discharged close to the eye surface. It is substantially more difficult to do this when the drug is self-administered. Gauging such short distances is physiologically difficult due to the inability to focus, and in addition the anticipation of the impacting drop often causes a blink and subsequent loss of portions of the drop. As a result, the user may inadvertently permit the dropper tip to contact the eye surface.

In any event, small amounts of eye liquids can thus be inadvertently permitted to commingle with the liquid of the drop to be delivered. Thus, when the pressure on the delivery container forcing the drop out is relieved, a small amount of the mixed liquids may be drawn back into the container. With time the bacteria originally present in the eye, both normal and pathological, will be permitted access to a medium which may cause them to proliferate. Thus, subsequent drops of medication may reintroduce to the eye either excessive levels of typically present bacteria, or large numbers of pathogens. Neither situation is acceptable.

To cope with the problems of contamination, drug manufacturers often introduce an anti-bacterial agent to the drug container. In most cases, this agent or preservative can be very effective at suppressing the growth of bacterial contaminants within the container. Unfortunately, there exists a significant population of patients for whom these preservatives represent ocular irritants, or in more severe cases, cause allergic reactions. Such untoward ocular reactions prevent such patients from using the drug in this kind of packaging. For these patients, single-use, non-preserved drug packaging is a partial answer, but at significantly increased cost and inconvenience.

Of course, similar problems are encountered with other drop-administered medicines, for example, for the ear or nose.

Container contamination can also be the result of particulate matter being drawn back into the container with the liquid in the dropper tip that has not been delivered as a drop. Over several drop deliveries in, for example, dusty conditions, a significant accumulation of dust in the container is possible. If the liquid to be delivered needs to be ultrapure as, for example, in certain microelectronic applications, such accumulation could raise a serious problem.

FLOW RATE

Dosage of drugs administered as drops is regulated on the basis of the number of drops to be applied. Formation of the drops is directly related to flow rate of the liquid from the container. The drops themselves fall from the dropper tip when the weight of the pendant drop exceeds the surface tension forces holding the drop to the dropper tip. In the ideal case, each drop should be identical to the previous one. In practice, however, other factors intervene to cause significant variation in drop size. One of the most significant factors is the rate of drop formation. If the drop is formed rapidly, more liquid can be "injected" into the body of the drop as it is beginning to break free. These drops will be larger, and thus will carry more drug, than if the container is squeezed very slowly. In extreme circumstances, drug may be ejected in a steady stream.

While this is a minimal problem when the drugs are delivered by a trained professional, it becomes significant when the drugs are delivered by the patients themselves. The flow rate, which is directly related to the finger pressure while squeezing, cannot be easily controlled. The visual clue, that is, the growth of the drop itself, cannot be readily observed if the eye is about to receive the same drop or if the dropper is not positioned in the line of sight in use.

The problem of delivery control is not restricted to ophthalmic drugs, of course, and there is a clear need for controllable addition devices in a wide range of, for example, pharmaceutical dispensing applications.

DESCRIPTION OF THE INVENTION

In the metering device defined in the present invention there is an inherently greater resistance to liquid flow than in a metering device of the prior art. For this reason, it becomes most difficult to produce a continuous stream of liquid by squeezing the container. This resistance to liquid flow also tends to damp out the natural variations in squeezing force that occur from moment to moment during use of a metering device of this type. As a result, the sequential drops metered from such a device tend to have a much more uniform size.

It is therefore an object of this invention to provide a flow metering device in which the problems of contamination and uncontrolled flow rate are substantially reduced.

It is a further object of this invention to provide a dropper for ocular medicines that is protected from inadvertent bacterial contamination and thus permit a significant reduction or the complete elimination of preservatives in the medicine.

It is another object of the invention to provide a liquid metering and dispensing device in which a liquid, such as a medicine, is dispensed as substantially uniform drops.

The above objects are provided by a device for dispensing a liquid in drop form which comprises a container having a dropper tip comprising a passage-way for ingress of air to and egress of liquid from the device, the passageway communicating between the body of the container and an orifice, means for temporarily reducing the volume of the container and, disposed within the dropper tip, across the passageway and adjacent the orifice, a composite microporous membrane with pores of a size to resist the passage of undesired contamination, the membrane having a liquophilic portion permitting delivery of metered drops of a liquid to a desired location outside the container, and a liquophobic portion adapted to resist the passage of such liquid but to permit the passage therethrough of air being intersected by the membrane and portions. The surface area of the liquophilic portion is so selected as to provide an appropriate drop dispensing rate and avoid a stream of liquid from emerging from the dropper tip.

The membrane is sealed to the inside surface of the dropper within the tip region so as to prevent the passage of liquid around, as opposed to through, the membrane.

The membrane comprises two components in side-by-side or juxtaposed relationship. One component has a liquophobic character, that is, it resists the passage of liquids. The other component has a liquophilic character, that is, liquids pass through it readily. Thus, liquids exiting the container through the porous membrane will pass exclusively through the liquophilic component and will be rejected by the liquophobic component. Liquids being sucked back into the container will pass exclusively through the liquophilic component. However, air will flow into the container to replace the expelled liquid through the liquophobic side.

THE CONTAINER

In use, the container functions as a reservoir for the liquid to be dispensed. It is provided with means to temporarily to reduce its volume, typically by providing that at least part of the container is elastically deformable. Thus, pressure on a deformable portion of the container will reduce the effective volume and force the liquid contained therein out of the container when it is appropriately oriented.

After a desired number of drops have been expelled from the container and the deforming pressure is removed, the liquid below the membrane in the tip is drawn back into the container. It is preferred that this occurs as a continuous column, that is, no droplets should break away and be left behind in the tip area. Such droplets could be a hospitable environment for bacterial growth and as such should be avoided so far as possible. Making the volume of the tip area very small helps to minimize this problem. It is, therefore, particularly preferred that the volume between the orifice of the dropper and the surface of the composite membrane be as small as possible. Volumes of the order of from about 0.001 to about 0.15 $cm^3$ are suitable and most preferred are volumes of from about 0.05 to about 0.1 $cm^3$.

The tip area of the dropper can be designed to provide membrane support by various means including, for example, a series of ribs on the inside surface of the dropper tip and/or an interior beading providing a seating surface to which the membrane can be bonded. Care should, however, be exercised to ensure that such support devices do not impede or distort the flow of metered drops from the device. Support could also be provided by the provision of a transverse septum or bar that would help resist any tendency of the membrane to deform under pressure.

WETTING OF POROUS MEDIA

The wettability or liquophilicity of a porous structure, e.g., a membrane, is a function of that structure's critical wetting surface tension (CWST) (discussed below) and the surface tension of the applied liquid. If the CWST is at least as high as the surface tension of the liquid, the liquid will spontaneously wet the porous structure, which may be termed "liquophilic" with respect to that liquid. Conversely, if the CWST is lower than the surface tension of the liquid then it will not be wet and will be liquophobic with respect to that liquid.

When a liquid is brought into contact with the upstream surface of a porous medium and a small pressure differential is applied, flow into and through the porous medium may or may not occur. A condition in which no flow occurs is that in which the liquid does not wet the material of which the porous structure is made.

A series of liquids can be prepared, each with a surface tension about 3 dynes/cm higher compared with the one preceding. A drop of each may then be placed on a porous surface and observed to determine whether it is absorbed quickly, or remains on the surface. For example, applying this technique to a 0.2 µm porous polytetrafluoroethylene (PTFE) membrane, instant wetting is observed for a liquid with a surface tension of about 26 dynes/cm. However, the structure remains unwetted when a liquid with a surface tension of about 29 dynes/cm is applied.

Similar behavior is observed for porous media made using other synthetic resins, with the wet/unwet values dependent principally on the surface characteristics of the material from which the porous medium is made and, secondarily, on the pore size characteristics of the porous medium. For example, fibrous polyester, specifically polybutylene terephthalate (hereinafter "PBT") sheets which have pore diameters less than about 20 μm will be wetted by a liquid with a surface tension of about 50 dynes/cm, but will not be wetted by a liquid with a surface tension of about 54 dynes/cm.

In order to characterize this behavior of a porous membrane, the term "critical wetting surface tension" (CWST) is defined as follows. The CWST of a porous medium may be determined by individually applying to its surface a series of liquids with surface tensions varying by about 2 to about 4 dynes/cm, and observing the absorption or non-absorption of each liquid. The CWST of a porous medium, in units of dynes/cm, is defined as the mean value of the surface tension of the liquid which is absorbed and that of a liquid of neighboring surface tension which is not absorbed. Thus, in the examples of the two preceding paragraphs, the CWST's are about 27.5 and about 52 dynes/cm, respectively.

In measuring CWST, a series of standard liquids for testing is prepared with surface tensions varying in a sequential manner by about 2 to about 4 dynes/cm. Ten drops from each of at least two of the sequential surface tension standard liquids are independently placed on representative portions of the porous medium and allowed to stand for 10 minutes. Visual observation is made after 10 minutes. Wetting is defined as absorption into the porous medium by at least nine of the ten drops within 10 minutes. Non-wetting is defined by non-absorption or non-wetting of at least nine of the ten drops in 10 minutes. Testing is continued using liquids of successively higher or lower surface tension, until a pair has been identified, one wetting and one non-wetting, which are the most closely spaced in surface tension. The CWST is then within that range and, for convenience, the average of the two surface tensions is used as a single number to specify the CWST.

A number of alternative methods for contacting porous media with liquids of sequentially varying surface tension can be expected to suggest themselves to a person knowledgeable of physical chemistry after reading the description above. One such involves floating a specimen on the surfaces of liquids of sequentially varying surface tension values, and observing for wet-through of the liquid or, if the fiber used is more dense than water, observing for sinking or floating. Another means would clamp the test specimen in a suitable jig, followed by wetting with the test liquids while applying varying degrees of vacuum to the underside of the specimen.

Appropriate solutions with varying surface tension can be prepared in a variety of ways; however, those used in the development of the product described herein were:

| Solution or fluid | Surface Tension range, dynes/cm |
| --- | --- |
| Sodium hydroxide in water | 94–110 |
| Calcium chloride in water | 90–94 |
| Sodium nitrate in water | 75–87 |
| Pure water | 72.4 |
| Acetic acid in water | 38–69 |
| Ethanol in water | 22–35 |
| n-Hexane | 18.4 |

-continued

| Solution or fluid | Surface Tension range, dynes/cm |
| --- | --- |
| FC77 (3M Corp.) | 15 |
| FC84 (3M Corp.) | 13 |

LIQUOPHILIC MEDIUM

Suitable materials for the liquophilic medium include forms of polyamides, polyvinylidene fluoride, and cellulose compounds, such as nitrocellulose and mixed esters of cellulose, as well as glass fiber mats with suitable binders. Hydrophilic, microporous polyamide membranes, particularly nylon 66 membranes, are especially preferred.

A preferred microporous, hydrophilic nylon 66 membrane material having high binding capacity, uniformity, controlled pore size, and high surface area is Biodyne ™, available from Pall Corporation or one of the hydrophilic membranes described in U.S. Pat. No. 4,340,479.

Another preferred membrane useful as the liquophilic medium is the CARBOXYDYNER ® membrane, also available from Pall Corporation. CARBOXYDYNER ® is a hydrophilic, microporous, skinless nylon 66 membrane with controlled surface properties formed by the co-casting process described in U.S. Pat. No. 4,707,266, as discussed below, specifically by cocasting nylon 66 and a polymer containing an abundance of carboxyl groups to form a membrane having controlled surface properties characterized by carboxyl functional groups at its surface.

Polyvinylidene fluoride membranes are not inherently water-wettable but can be rendered such by an appropriate surface treatment. Microporous, polyvinylidene fluoride membranes which have been treated to render them hydrophilic are commercially available. As discussed above, wettability or liquophilicity is a function of the CWST of the porous membrane and the surface tension of the liquid. Wettability may also be expressed in terms of intrusion pressure required for liquid to penetrate into the pores of the membrane. Membrane materials which are particularly preferred have intrusion pressures of, or close to, zero for the liquids with which they are used.

These hydrophilic, microporous, substantially alcohol-insoluble polyamide membranes with controlled surface properties are formed by cocasting an alcohol-insoluble polyamide resin with a water-soluble, membrane-surface-modifying polymer having functional polar groups. Like the preferred hydrophilic, microporous nylon membranes which do not have controlled surface modified polar groups present, the polyamide membranes of the present invention having controlled surface properties are also skinless; that is, they are characterized by through pores extending from surface to surface which are of substantially uniform size and shape.

LIQUOPHOBIC MEDIUM

The term "liquophobic" as used herein is effectively the obverse of the term "liquophilic", that is, a porous liquophobic material has a CWST lower than the surface tension of the applied liquid and is not readily or spontaneously wetted by the applied liquid(s). Liquophobic materials are characterized, then, by a high contact angle between a drop of liquid placed on the surface and the surface. Such a high contact angle indicates poor wetting.

Another way of expressing the suitability of a material for use as the liquophobic component of the instant invention relates to the wetting resistance characteristics of the material. A suitable material should be capable of resisting a liquid intrusion pressure greater than the pressure that can be generated by manual squeezing of the dispensing bottle. Suitable materials include polyolefins, such as polypropylene, polyhalogenated polyolefins, particularly perfluorinated polyolefins, such as polytetrafluoroethylene, and polyvinylidene difluoride, as well as sulfones. Polytetrafluoroethylene is a preferred polymer and surface modified polyvinylidene difluoride, particularly a fluoropolymer-grafted microporous polyvinylidene difluoride membrane or similarly surface modified polyamides are most preferred. Particularly preferred is a polyamide which has been surface modified to have a CWST of less than about 29 dynes/cm.

The liquophobic component of the membrane typically has a CWST of less than about 35 dynes/cm and typically from about 20 dynes/cm to about 30 dynes/cm. By contrast, the liquophilic component of the membrane has a CWST of at least about 50 dynes/cm, such as from about 70 dynes/cm to about 100 dynes/cm, and preferably from about 72 dynes/cm to about 95 dynes/cm.

The Composite Membrane

The composite membrane used in the present invention has both a liquophilic preferably hydrophilic component and a liquophobic preferably hydrophobic component. Most frequently, these will be bonded together along the line of contact so as to form a single unit with the components in juxtaposed or side-by-side (as opposed to superposed or face-to-face) relationship to one another. Part of the composite will, preferably, be hydrophilic with respect to the liquid to be dispensed with the device and the other part will be hydrophobic with respect to that same liquid.

It is to be understood, however, that the term "composite membrane" is also intended to cover the functional equivalent of such a membrane where the two components are not physically joined but act to close off separate but adjacent exit passages from the device. One example would be provided by a device with a dropper tip having a transverse septum or bar in the area of the dropper tip dividing the exit passageway effectively in two. With such a device each membrane could be sealed to the septum or bar and the inside wall of the tip and there would be no need for bonding the two membranes together. Indeed, this configuration might confer useful support benefits for the membranes.

Both components of the membrane have a pore size adapted to resist passage of an undesired contaminant. Most frequently, in the medicinal context, this will be bacterial contamination. In this context, for the liquophilic component, pore sizes of from about 0.04 to about 0.65 $\mu$m are suitable. Preferred are pore sizes of from about 0.01 to about 0.45 $\mu$m and most preferred are pore sizes of from about 0.15 to about 0.2 $\mu$m. The liquophobic component, however, generally has a pore size of from about 0.01 to about 0.45 $\mu$m with from about 0.04 to about 0.2 $\mu$m preferred and from about 0.1 to about 0.2 $\mu$m most preferred. If particulate contamination is the main concern, the pore sizes can be redefined accordingly.

The liquophilic and liquophobic membranes can be attached within the dropper tip by known techniques, such as heat welding or ultrasonic welding. For proper function the formation of a bacteria-tight seal at the entire perimeter of the weld is critical. It is also necessary to form a bacteria-tight seal at the junction of the liquophilic and liquophobic membranes. This can be achieved by bonding the membranes together in a separate operation, with the minimum overlap required to assure a complete seal. Ultrasonic welding techniques are often preferred for this operation though good results can be obtained by heat sealing. Overlaps of less than or equal to about 3 mm (0.12 in) are preferred, and less than or equal to about 1 mm (0.039 in) are most preferred.

After bonding the membranes, discs of the membrane pairs may be punched out using conventional die punching techniques. The position of the die above and below the bond line can be used to set the relative proportions of the liquophilic and liquophobic areas of the membranes.

After punching, the discs may be transferred to the base of the dropper tip and welded in position. Alternatively, two separate regions of the dropper base may be defined and individual components of the liquophilic and liquophobic membranes welded thereto.

It is found that the bonding operation is often much simplified if the substrate membrane of both the liquophilic and liquophobic components is the same. This can be achieved by surface modification of chemically identical or closely related polymeric membranes to give liquophilic and liquophobic components which are then joined together to form the composite membranes useful in the device of the invention. Composite membranes in which both components are suitably surface-modified polyamides are particularly preferred.

The surface area of the composite membrane can be divided between liquophilic and liquophobic components in any convenient proportion. However, the proportions should be consistent with the functions that the components have to fulfill. The liquophilic membrane should be of such a size that the liquid within the container will be dispensed in drops at an appropriate rate. Too large an area could result in a high rate of flow or even, in extreme cases, a stream of liquid. On the other hand, too small an area would result in a very low drop delivery or dispensing rate.

METERING FUNCTION OF THE HYDROPHILIC COMPONENT

An important aspect of the present invention is the provision of a deformable dropper bottle that meters out drops at a carefully regulated flow rate. When the liquophilic portion of the membrane selected is hydrophilic with respect to the liquid to be dispensed and has a porosity that is fine enough to exclude bacteria, the factor that controls the rate at which drops are dispensed is the surface area of the liquophilic, preferably hydrophilic portion of the membrane. This drop formation rate is largely independent of the pressure differentials caused by any deformations of the dropper bottle likely to be encountered in the normal use of such devices. This is, of course, a significant safety factor since the dropper bottle, by design and intent, will be for use by medically untrained people with varying interpretations of the level of pressure needed to express one drop from the bottle.

The hydrophilic membrane surface area that is best suited to produce an appropriate liquid flow rate in the above circumstances is found to be about from about 20 mm² to about 90 mm², and preferably from about 40 mm² to about 50 mm².

The liquiphobic, preferably hydrophobic component should be large enough to accommodate relatively easy but controlled access of air to replace the liquid dispensed. It is found that with devices of the size normally employed for eye droppers, satisfactory results may be obtained when the proportion of the liquophilic component is from about 50 to about 70% of the total surface area of the composite membrane. This provides sufficient surface area of the liquophilic, preferably hydrophilic, component to ensure a satisfactory flow rate from the dropper battle when it is deformed. Particularly preferred, however, are membranes where about 60 to about 70% of the surface area is provided by the liquophilic component. It is recognized, however, that some applications may require proportions outside the above ranges.

DESCRIPTION OF THE DRAWINGS

FIG. 2 is a plan view of the microporous membrane shown separate from the container.

DESCRIPTION OF PREFERRED EMBODIMENTS

Figure 1:
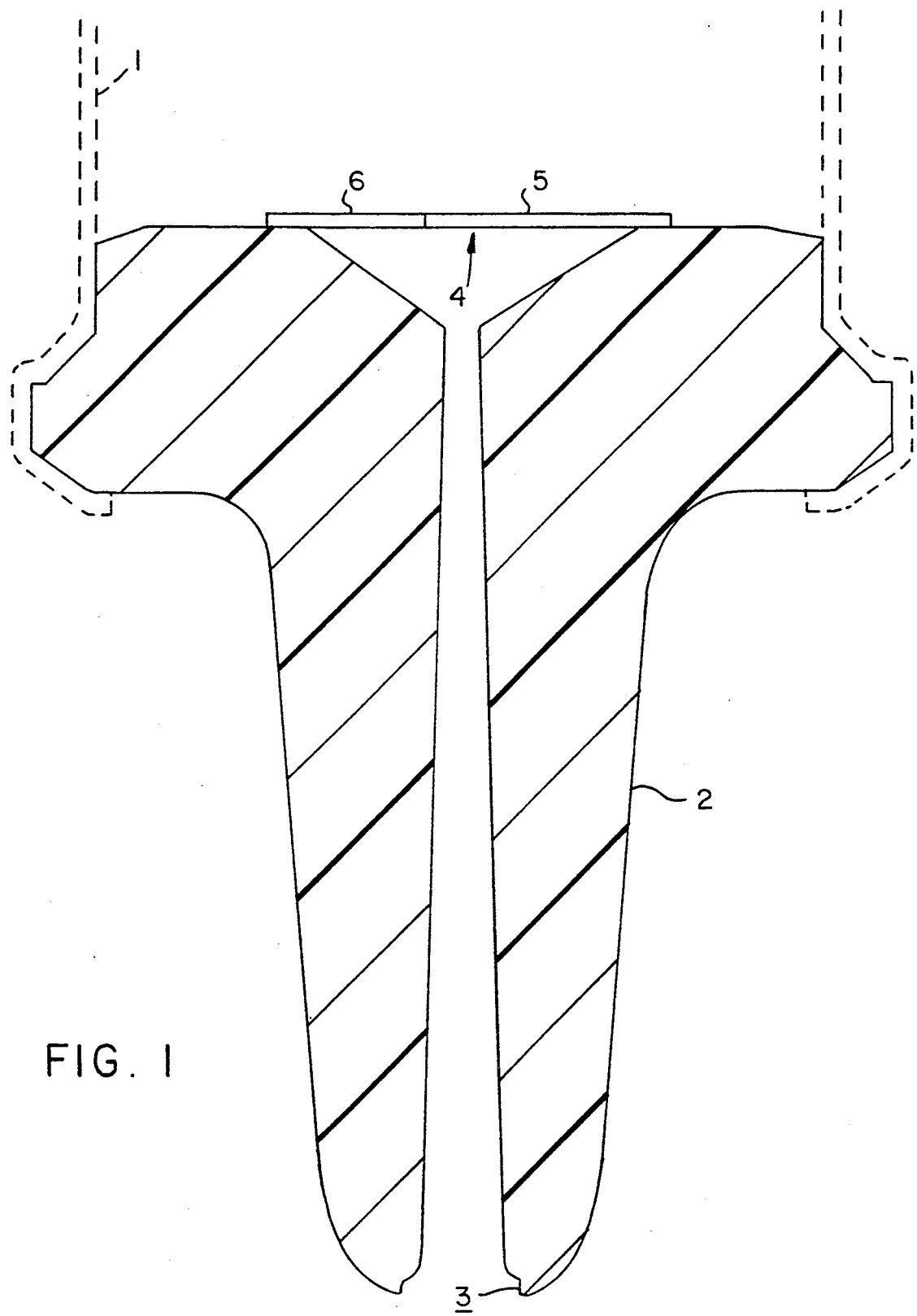
FIG. 1 is a diagrammatic cross-section of the tip and adjacent portions of a deformable container according to the invention.

The invention is further described with specific reference to the drawings which illustrate a preferred embodiment of the invention. In the drawings, FIG. 1 represents a partial cross-section of a dropper according to the invention. FIG. 2 represents a plan view of a composite membrane according to the invention.

In FIG. 1, a container (partially shown in dotted outline as 1) has a dropper tip 2 which terminates in an orifice 3. Disposed in the dropper tip 2 adjacent the container is a membrane 4 sealed to the surface of the dropper tip 2. The membrane 4 has a generally circular configuration conforming to the dimensions of the opening in the dropper tip 2. The membrane 4 is a composite of two components in side-by-side relationship: a liquophilic component 5 and a liquophobic component 6 sealed at their line of contact to form a unitary disc-shaped composite membrane. In use, the container is inverted, that is to say, placed with its dropper tip downwards, and squeezed. This reduces the effective volume of the container and creates a pressure differential between the inside and the outside of the container such that the liquid contained therein is expelled. The liquid is typically a drug in an aqueous solution intended for treatment of eye disorders. The drug solution wets and then passes through the liquophilic membrane into the dropper tip. As the pressure is maintained, the liquid emerges from the dropper tip orifice and begins to form a pendant drop. When used for administering ocular medicine, it is intended that this drop fall into the eye of the patient. As the drop reaches critical size, it breaks away from the dropper tip orifice and falls into the eye. When the squeezing pressure on the container is removed, a differential pressure is created between the outside of the container and the inside, as the elastic walls of the container attempt to return to their original shape. This differential pressure causes the liquid remaining in the dropper tip to be drawn back towards the inside of the container. In doing so, the liquid must pass through the liquophilic component of the membrane. The dropper tip is designed so that substantially all if not all of the liquid remaining after the drop is dispensed is drawn back into the container. As the retreating liquid/air interface in the dropper tip reaches the liquophilic membrane, flow through the liquophilic membrane halts. This is because significantly higher pressure than is available from recovery of the elastically deformed walls of the container, which reverses the pressure differential referred to above, is required to drive air through the wetted liquophilic membrane. Incoming air, however, is necessary to compensate for the volume of the drug dispensed. This can enter the container through the adjacent liquophobic membrane. Thus, sufficient air will enter the container via the liquophobic membrane to equalize the pressure inside and out.

In the event that the liquid in the dropper tip has become contaminated, for example, by contact with bacteria from the patient's optical fluids, the bacterial component is filtered by the liquophilic component as the rest of the liquid is drawn back into the container. Thus, liquid and air re-entering the container from the dropper tip area are filtered free of bacterial contamination.

Since the internal volume and shape of the dropper tip are selected to minimize the possibility of any retained liquid, any bacteria present and trapped on the liquophilic and liquophobic membrane components are thus exposed to the air. Such exposure may inhibit growth such that subsequent drops dispensed from the container will be either free or substantially free of contaminants previously entrained in the dropper tip. Thus, the tip will be returned substantially to its pre-contamination state with each cycle of use. If contamination is likely to have occurred and it is imperative that no amount of bacteria be returned to the eye, then the first drop or drops of drug may be discarded so as to purge the tip. Experiments in which the dropper has been seeded with known levels of bacteria suggest that this procedure is effective.

EXPERIMENTAL DATA

To test the concept, two dropper bottles and tips were constructed using a 0.2 μm rated Biodyne ® nylon 66 membrane as the liquophilic segment, and 0.02 μm rated polytetrafluoroethylene membrane as the liquophobic segment. The membranes were first bonded together along their midlines using a Branson ultrasonic welder with a gold booster and a flat 2"×2" welding horn. An approximately 1 to 3 mm overlap was formed at the weld line. The dropper tips were modified by filling the excess space between the membrane and the tip with an epoxy compound, resulting in a volume of approximately 0.1 cm³. Discs were then cut from the resulting composite strip and ultrasonically welded at their perimeters to the base of the dropper tips. In these tips approximately 60% of the total membrane area was occupied by the liquophilic membrane.

The tips were then aseptically inserted into dropper bottles containing an ophthalmic drug timolol maleate, but with no preservatives included.

A solution containing approximately $1 \times 10^5$ per milliliter of p. aeuriginosa was prepared. Bottle 1 was oriented tip upright, squeezed, and held. Then, an aliquot of 100 μl of the p. aeurioinosa solution was injected into the opening of the dropper tip using a microsyringe.

The pressure on the bottle was then released, and the 100 μl aliquot was observed to draw back into the bottle. The second bottle, bottle C, did not have any bacteria solution injected and was kept as a control.

Ten minutes after the inoculation of bottle 1, a sequence of 4 drops of timolol maleate was squeezed out and each drop directed to fall into a quadrant of an agar plate (Q1 to Q4). Each drop was then spread by streaking across the quadrant with a sterile loop. One day later, the same procedure was repeated with another agar plate. This repetitive sampling was continued for 14 days. In parallel, the control bottle, bottle C, was sampled in the identical manner.

The data for the inoculated bottle, bottle 1, is shown below:

| DAY | COLONIES/QUADRANT | | | |
| --- | --- | --- | --- | --- |
|  | Q1 | Q2 | Q3 | Q4 |
| 10 min | 128 | 90 | 65 | 51 |
| 1st | 0 | 0 | 0 | 0 |
| 2nd | 0 | 0 | 0 | 0 |
| 3rd | 0 | 120[a] | 0 | 0 |
| 4th to 14th | 0 | 0 | 0 | 0 |

[a]Note: colonies seen were not p. aueroginisa.

The control bottle, bottle C, had zero counts for all days in all quadrants.

In this experiment, the 100 μl inoculation was observed to be drawn back into the bottle. Thus, the bacteria in the aliquot was presented to the composite membrane at the base of the dropper tip. Lack of *p. aeurioinosa* growth in the samples from days 1 to 14 demonstrates that none of the bacterial challenge reached the contents of the bottle.

The data from the 4 drop sequence taken 10 minutes after inoculation is a confirmation that *p. aeuriginosa* bacteria was present in the dropper tip and, in addition, that it would not flourish or could be purged by the removal of several drops.

In the discussion of the preferred embodiment illustrated in the drawings, a device adapted to dispense ocular medicine was taken as the paradigm. It is to be understood, however, that the device of the invention could be used for other purposes in which it is convenient to dispense the medicine in the form of drops such as, for example, medicine for the ears or the nose. In general, the medicine will be made up in an aqueous or saline solution; thus the terms liquophilic and liquophobic will most conveniently imply hydrophilic and hydrophobic, respectively. It is understood, however, that occasionally medicines are made up in a light oil and thus the broadest interpretation of liquophobic and liquophilic must embrace the use of such liquids as media for the application of the medicine.

The body of the container is provided with means for temporarily reducing the volume of the container. Typically, this will be by providing that at least part of the walls of the container are elastically deformable. Thus squeezing the container will temporarily reduce its volume. Alternative means such as a movable plunger or an inflatable insert in the container could be devised but are not generally preferred over the simplicity of the squeezable container.

We claim:

1. A device for dispensing liquids in drop form of substantially uniform size which comprises a container having a dropper tip including a passageway for ingress of air to and egress of liquid from said device, said passageway communicating between the container and an orifice in the dropper tip; means for temporarily reducing the volume of the container; and disposed within the dropper tip, across the passageway, a microporous composite membrane with pores of a size to resist passage of contaminants, said membrane having a liquophilic component permitting delivery of drops of a liquid to a desired location outside the container and a liquophobic component adapted to resist the passage of such liquid but to permit the passage therethrough of air, the surface area and pore size of said liquophilic component being so selected as to meter liquid being dispensed in drop form and avoid a stream of liquid from emerging from the dropper tip during normal use, said passageway being intersected by said membrane and communicating with both the liquophilic and liquophobic components.

2. A device according to claim 1 wherein and the pore size of the liquophoilic component of the membrane is from about 0.04 to about 0.65 μm.

3. A device according to claim 1 wherein the pore size of the liquophobic component of the membrane is from about 0.01 to about 0.45 μm.

4. A device according to claim 1 wherein the liquophilic component comprises from about 50 to about 70% of the surface area of the membrane.

5. A device according to claim 1 wherein the volume between the composite membrane and the dropper tip orifice is from about 0.001 to about 0.15 $cm^3$.

6. A device according to claim 1 adapted to dispense an aqueous solution wherein the liquophobic component has a critical wetting surface tension of less than 35 dynes/cm.

7. A device according to claim 6 wherein the liquophilic component of the composite membrane has a critical wetting surface tension of at least 72 dynes/cm.

8. A device according to claim 6 wherein said aqueous solution includes a medicine.

9. A device according to claim 1 wherein the liquophilic component is made from a surface-modified microporous nylon polymer membrane.

10. A device according to claim 1 wherein the liquophobic component is made from a surface-modified microporous polyvinylidene fluoride membrane.

11. A device according to claim 1 wherein the container has elastically deformable sides.

12. A device according to claim 1 wherein the porosity of the composite microporous membrane is suitable for resisting the passage of bacterial contamination and the liquophilic component has a surface area of from about 20 $mm^2$ to about 90 $mm^2$.

13. A device according to claim 1 wherein said liquophilic component comprises a surface-modified microporous nylon membrane and said liquophobic component comprises a surface-modified microporous polyvinylidene fluoride membrane.

14. A device according to claim 1 wherein said liquophilic component comprises a surface-modified polyamide membrane having a CWST of at least about 50 dynes/cm and said liquophobic component comprises a surface-modified polyamide having a CWST of less than about 35 dynes/cm.

15. A device according to claim 14 wherein the CWST of said liquophilic component is at least about 72 dynes/cm and said liquophobic component is less than about 29 dynes/cm.

16. A device according to claim 1 wherein said orifice comprises a single orifice.

17. A device according to claim 1 wherein said liquophilic and liquophobic components are arranged in juxtaposed relationship.

18. A device according to claim 1 wherein the liquophilic component comprises a surface treated polyvinylidene fluoride membrane.

19. A device according to claim wherein each of the liquophilic and liquiphobic components comprise polyvinylidene fluoride membranes.

20. A device according to claim 1 wherein said liquophilic component comprises a surface-treated polyvinylidene fluoride membrane having a CWST of at least 50 dynes/cm and said liquophobic component comprises a polyvinylidene fluoride membrane having a CWST of less than about 75 dynes/cm.

21. A device for dispensing liquids in drop form of substantially uniform size which comprises an elastically deformable container having a dropper tip with a passageway therethrough for ingress of air to and egress of liquid from said device, said passageway terminating in an orifice and, disposed within the dropper tip and across the passageway, a composite microporous membrane with pore sizes less than 0.45 μm, said membrane comprising a hydrophilic component and a hydrophobic component, said hydrophilic component providing from about 60 to about 70% of the surface area of the composite membrane, said hydrophilic component having a surface area so selected as to meter liquid being dispensed in drop form and avoid a stream of liquid from emerging from the dropper tip during normal use, and said passageway being intersected by said membrane and communicating with both of said hydrophilic and hydrophobic components.

22. A device according to claim 21 wherein a composite microporous membrane has first and second components bonded together in side-by-side relationship, the first component having a surface area of from about 40 mm$^2$ to about 50 mm$^2$, an average pore size of from about 0.15 to about 0.25 μm, and a CWST of at least about 72 dynes/cm and being made from a surface-modified polyamide; and the second component being made from a polyamide that has been surface-modified to produce a CWST of less than about 35 dynes/cm and having an average pore size of from about 0.1 to about 0.2 μm.

23. A device according to claim 22 wherein the volume between the orifice of the dropper and the surface of the composite membrane closest to the tip is from about 0.05 to about 0.1 cm$^3$.

24. A device for dispensing liquids in drop form of substantially uniform size which comprises a container having a dropper tip including a passageway for ingress of air to and egress of liquid from said device, said passageway communicating between the container and an orifice in the dropper tip and, disposed within the dropper tip across the passageway, a microporous membrane with pores of a size to resist passage of contaminants, said membrane having a liquophilic component permitting delivery of drops of a liquid to a desired location outside the container, and a liquophobic component adapted to resist the passage of such liquid but to permit the passage therethrough of air, said passageway being intersected by said membrane and communicating with both of said liquophilic and liquophobic components, the surface area and pore size of the liquophilic component being selected so as to meter the liquid being dispensed in drop form and avoid a stream of liquid from emerging from the dropper tip during normal use.

25. A device according to claim 24 wherein the porosity of the microporous membrane is selected so as to resist the passage of bacterial contaminants and the surface area of the hydrophilic component is from about 20 mm$^2$ to about 90 mm$^2$.

* * * * *

UNITED STATES PATENT AND TRADEMARK OFFICE
CERTIFICATE OF CORRECTION

PATENT NO. : 5,219,101
DATED : June 15, 1993
INVENTOR(S) : Matkovich et al.

It is certified that error appears in the above-indentified patent and that said Letters Patent is hereby corrected as shown below:

Column 12, Line 19, delete "and";

Column 12, Line 20, change "liquophoilic" to --liquophilic--;

Column 13, Line 9, after "claim" insert --1--;

Column 13, Line 17, change "75" to --35--.

Signed and Sealed this

Twenty-eighth Day of November 1995

Attest:

BRUCE LEHMAN

Attesting Officer      Commissioner of Patents and Trademarks